United States Patent [19]
Ward et al.

[11] Patent Number: 5,279,166
[45] Date of Patent: Jan. 18, 1994

[54] SELF-ALIGNING BIAXIAL LOAD FRAME

[75] Inventors: Michael B. Ward; Jonathan S. Epstein; W. Randolph Lloyd, all of Idaho Falls, Id.

[73] Assignee: EG&G Idaho, Inc., Idaho Falls, Id.

[21] Appl. No.: 953,039

[22] Filed: Sep. 29, 1992

[51] Int. Cl.⁵ .............................................. G01N 3/08
[52] U.S. Cl. ........................................ 73/794; 73/856
[58] Field of Search ................ 73/794, 795, 796, 797, 73/798, 856

[56] References Cited
U.S. PATENT DOCUMENTS
4,895,027  1/1990  Manahan, Sr. ................. 73/794 X

*Primary Examiner*—Jerry W. Myracle
*Attorney, Agent, or Firm*—Alan D. Kirsch

[57] ABSTRACT

An self-aligning biaxial loading apparatus for use in testing the strength of specimens while maintaining a constant specimen centroid during the loading operation. The self-aligning biaxial loading apparatus consists of a load frame and two load assemblies for imparting two independent perpendicular forces upon a test specimen. The constant test specimen centroid is maintained by providing elements for linear motion of the load frame relative to a fixed crosshead, and by alignment and linear motion elements of one load assembly relative to the load frame.

6 Claims, 2 Drawing Sheets

SELF-ALIGNING BIAXIAL LOAD FRAME

CONTRACTUAL ORIGIN OF THE INVENTION

The United States Government has rights in this invention pursuant to Contract No. DE-AC07-76ID01570 between the U.S. Department of Energy and EG&G Idaho, Inc.

BACKGROUND OF THE INVENTION

This invention relates to a biaxial loading apparatus and more particularly to a self-aligning biaxial load fixture for applying orthogonal axial loads to a test specimen while maintaining a constant specimen centroid during the loading operation.

Recent developments in carbon-carbon composites, ceramics and alloys have substantially advanced the state of the art and have resulted in the development of interest in such materials for use in structural applications. Currently, there is no way to test these materials in a multi-axial stress state without imparting some undesirable stresses to the materials being tested, due to alignment problems in the apparatus loading the test specimen.

Considerable effort has been made in an attempt to satisfy a long-felt need for determining properties of brittle materials such as carbon-carbon composites, ceramics and alloys. Most efforts have focused on compressive, torsional and tensile testing. A need exists for expanding capabilities to include biaxial testing, that is, axial compressive and/or tensile testing along orthogonal axes. Because brittle materials are extremely sensitive to misalignment during testing, it has not been possible to test these types of materials in orthogonal axial directions without introducing unacceptable moments in the test specimen. These types of tests are imperative, however, for developing design guidelines for structural applications of brittle materials. Accordingly, a means is needed that will maintain alignment of a brittle test specimen continually during a test involving biaxial loading.

Biaxial load testing machines are known in the art which apply a monoaxial load to a test piece from orthogonal directions. U.S. Pat. No. 3,797,303 describes such a device which applies monoaxial compression load to a test specimen. In this invention, the device provides two orthogonal compression assemblies carried independently on guides. However, with this type of device some amount of undesirable moments to the test specimen can occur during compression loading, resulting in inaccurate load bearing data of the specimen.

Also, a triaxial compression test apparatus is shown in U.S. Pat. No. 4,615,221 which tests cylindrically-shaped samples by imparting a compressive force along the longitudinal axis of the sample. This compressive force then creates a second force along the axial axis of the cylindrical sample through the use of hydraulic fluid surrounding the object. However, the application of this device is limited to compressive testing of cylindrical samples.

U.S. Pat. No. 4,686,860 describes a grip system for transmitting an uniaxial load to a ceramic specimen without introducing bending stresses into the specimen. In this device a multiplicity of hydraulic piston assemblies are equally spaced in a hydraulic housing assembly on a circle about the centerline of the tensile specimen. Use of a hydraulic fluid as a distribution medium to divide the applied uniaxial load into a multiplicity of equal parts counteracted by the circular array of miniature pistons is a key feature of this invention. However, frequently it is desired to apply a multiaxial load to a test specimen, including both tensile and/or compression testing.

A hydrostatic self-aligning axial/torsional mechanism is described in U.S. Pat. No. 4,928,532 for testing specimens without introducing bending moments induced by other testing means. The test specimen can be tested by this invention for uniaxial strength, torsional strength, or a combination of the two. However, this invention does not test for compressive and/or tensile axial strength from orthogonal directions and accordingly does not consider the inducement of bending moments in the test specimen during the loading operation. It should be noted that the term "biaxial" as used in U.S. Pat. No. 4,928,532 refers to a combined axial and torsional loading, whereas in the present invention the term "biaxial" is understood to mean axial loading along orthogonal axes.

Accordingly, it is an object of this invention to provide for a means to test the compressive and/or tensile axial strength of a specimen in orthogonal directions.

It is another object of this invention to provide a means for maintaining the orthogonal alignment of the test specimen during testing.

Another object of this invention is to provide a means for applying orthogonal axial stress to a specimen without inducing significant moments in the specimen.

Additional objects, advantages and novel features of the invention will become apparent to those skilled in the art upon examination of the following and by practice of the invention.

SUMMARY OF THE INVENTION

To achieve the foregoing and other objects, a self-aligning biaxial load frame is provided for use in testing the strength of specimens while maintaining a constant specimen centroid during the loading operation. The biaxial loading device consists of a load frame and two load assemblies for imparting two perpendicular forces upon a test specimen. The constant specimen centroid is maintained by providing means for linear motion of the load frame relative to a fixed crosshead, and by alignment and linear motion means for one load assembly relative to the load frame. The device is capable of providing tension:tension, compression:compression, or compression:tension axial forces to the test specimen while maintaining a constant specimen centroid during loading operations.

BRIEF DESCRIPTION OF THE DRAWINGS

The present invention is illustrated in the accompanying drawings where.

DETAILED DESCRIPTION OF THE INVENTION

Figure 1:
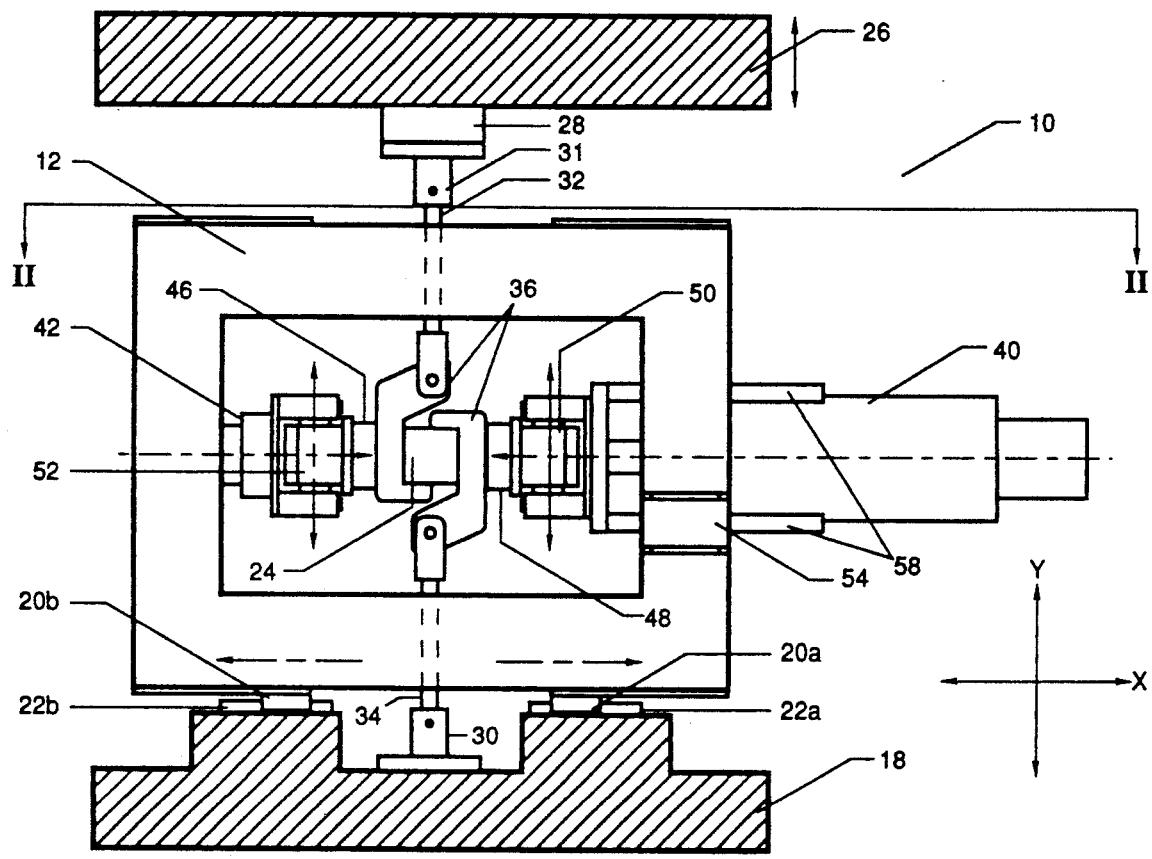
FIG. 1 is a elevational view partly in section of the self-aligning biaxial loading device in accordance with the present invention.

Referring now to the drawings in which like numerals represent like elements throughout the several views, the preferred embodiment of the present invention will be described. FIG. 1 shows a drawing depicting the self-aligning biaxial load device 10, which generally consists of a frame 12 and two orthogonal independent load assemblies. To facilitate an understanding of the present invention, orthogonal X- and Y-axes are shown in FIG. 1. The frame 12 is linearly movable relative to a fixed crosshead 18, preferably by means comprising a set of linear motions bearings 20a and 20b, and rails 22a and 22b. This permits the frame 12 to move in the X-axis direction during the loading operation. The Y-axis load assembly is capable of providing either compression or tension loading to a test specimen 24 along the Y-axis, while the X-axis load assembly provides either compression or tension loading to specimen 24 along the X-axis.

The Y-axis load assembly is comprised of a load actuator 26 for imparting a tension or compression load along the Y-axis. In the preferred embodiment of the present invention, load actuator 26 imparts the tension or compression load to the test specimen 24 via the of Y-axis load cell 28. Load cell 28 is connected to the load actuator 26 while a coupling 30 is attached to the fixed crosshead 18. Load cell 28 and coupling 30 are connected to load shafts 32 and 34 respectively, said load shafts 32 and 34 further being attached to a pair of grips 36. Depending upon the load testing being conducted, the grips 36 are either flexibly or rigidly attached to the load shafts. FIG. 1 illustrates a non-rigid connection between the load shafts and the grips so that a compression/shear load test can be conducted on the test specimen 24.

The X-axis load assembly includes a load actuator 40 for creating a tension or compression force along the X-axis. As shown in FIG. 1, load actuator 40 is aligned using alignment shafts 58 and alignment bearings 54 which provide for the aligned and nonrotational movement about the X-axis. The X-axis load assembly also includes X-axis load cell 42 oppositely located about the test specimen from said load actuator. Load cell 42 is rigidly attached to frame 12. In a preferred embodiment, spacers 46 and 48 are positioned between the load cell 42 and the pair of grips 36. Preferably the Y-axis dimension of the spacers is equal to or greater than the Y-axis dimension of the test specimen to prevent the rotation of the test specimen during the loading operation.

The self-aligning biaxial load device of the present invention is capable of providing tension:tension, compression:compression, or compression:tension axial forces to the test specimen while maintaining a constant specimen centroid during the specimen loading operation. To maintain the constant specimen centroid, linear motion bearing mechanisms 50 and 52 are provided in the X-axis assembly to permit the Y-axis movement of the test specimen during the loading operation. An example of a possible linear motion bearing mechanism would be a ball bushing bearing system. Additionally in the operation of the present invention, as previously stated, a set of linear motion bearings 20 and rails 22 permit the X-axis movement of the frame 12 thereby providing constant specimen centering during the loading operation.

Figure 2:
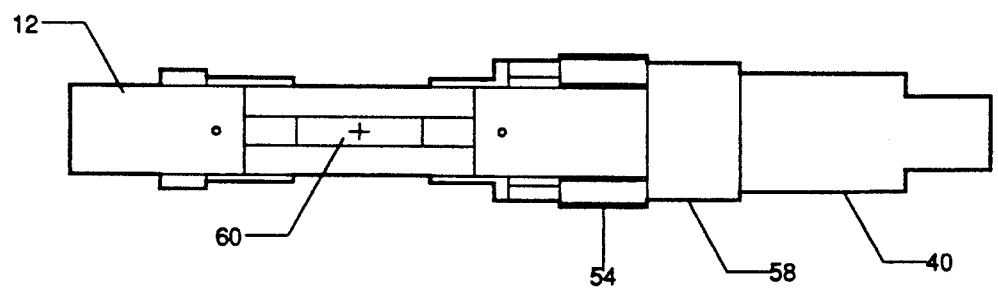
FIG. 2 is a cross-section view taken along the lines II—II of FIG. 1.

FIG. 2 shows a plan view of the frame 12 and X-axis load assembly with the Y-axis load assembly having been removed. As can be seen in FIG. 2, an opening 60 is provided in frame 12 through which the Y-axis load assembly is positioned. FIG. 2 shows the positioning of the alignment bearings 54 along each side of frame 12 for moving the X-axis crosshead and restricting the specimen from tilting or rotating off the X-axis.

Figure 3:
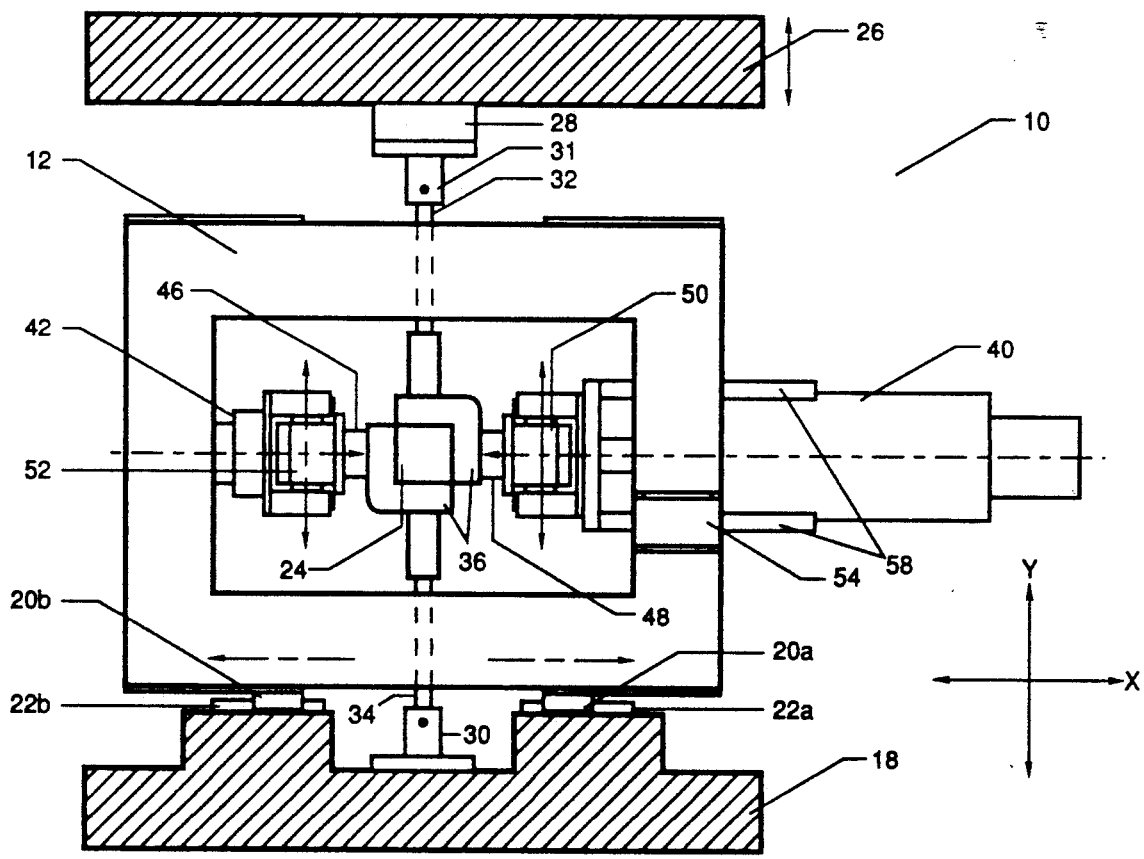
FIG. 3 depicts an alternate embodiment of the self-aligning biaxial loading device using grips for compressive:compressive load testing.

Referring now to FIG. 3 another embodiment of the present invention is shown. FIG. 3 illustrates how the pair of grips 36 can be rigidly connected to the load shafts 32 and 34 to provide for compression:compression load testing of a test specimen without introducing bending moments in the specimen. Alternatively, the grip assembly shown in U.S. Pat. Nos. 4,686,869 and 4,843,888 could be used with the present invention to provide for tension:tension testing of a specimen without introducing bending moments in the specimen.

The foregoing description of a preferred embodiment of the invention has been presented for purposes of illustration and description. It is not intended to be exhaustive or to limit the invention to the precise form disclosed, and obviously many modifications and variations are possible in light of the above teaching. The embodiments described explain the principles of the invention and practical application and enable others skilled in the art to utilize the invention in various embodiments and with various modifications as are suited to the particular use contemplated. It is intended that the scope of the invention be defined by the claims appended hereto.

The embodiments of this invention in which an exclusive property or privilege is claimed are defined as follows:

1. A self-aligning biaxial load testing device for testing specimens while maintaining a constant specimen centroid, comprising:
 (a) a load frame assembly having an opening through which a first loading assembly is positioned for providing a first axial force upon a test specimen;
 (b) a linearly movable second loading assembly mounted on said load frame assembly for providing a second axial force upon the test specimen, said second axial force being aligned in a direction perpendicular to the first axial force;
 (c) means for making it possible for the load frame assembly to move freely in a linear motion direction parallel to the second axial force direction;
 (d) means for making it possible for the second loading assembly to move freely in a linear motion direction parallel to the first axial force.

2. The device of claim 1 wherein said first and second axial forces are compressive axial forces upon said test specimen.

3. The device of claim 1 wherein first and second axial forces are tensile axial forces upon said test specimen.

4. The device of claim 1 wherein said first axial force for is tensile and said second axial force is compressive upon said test specimen.

5. The device of claim 1 wherein the first axial force is compressive and said second axial force is tensile upon the test specimen.

6. The device of claim 1 wherein the load frame assembly linear motion means is a ball bearing guide and rail system.

* * * * *